(12) United States Patent
Kaye (10) Patent No.: US 10,675,374 B2
(45) Date of Patent: Jun. 9, 2020

(54) INSECT TRAP

(75) Inventor: Mathew Varghese Kaye, West Midlands (GB)

(73) Assignee: Brandenberg Limited (GB)

( * ) Notice: Subject to any disclaimer, the term of this patent is extended or adjusted under 35 U.S.C. 154(b) by 654 days.

(21) Appl. No.: 13/994,703

(22) PCT Filed: Dec. 14, 2011

(86) PCT No.: PCT/GB2011/001719
§ 371 (c)(1),
(2), (4) Date: Oct. 14, 2013

(87) PCT Pub. No.: WO2012/080698
PCT Pub. Date: Jun. 21, 2012

(65) Prior Publication Data
US 2014/0026467 A1    Jan. 30, 2014

(30) Foreign Application Priority Data

Dec. 15, 2010 (GB) .................................. 1021293.4

(51) Int. Cl.
*A61L 9/20* (2006.01)
*A01M 1/14* (2006.01)

(52) U.S. Cl.
CPC ............... *A61L 9/20* (2013.01); *A01M 1/145* (2013.01)

(58) Field of Classification Search
CPC ............ A01M 1/04; A01M 1/06; A01M 1/08; A01M 1/106; A01M 1/145; A01M 2200/01; A61L 2/0047; A61L 2/10; A61L 9/20

USPC ....... 43/107, 111, 113, 114, 119, 132.1, 136, 43/138, 139, 141
See application file for complete search history.

(56) References Cited

U.S. PATENT DOCUMENTS 6,108,965 A * 8/2000 Burrows ............... A01M 1/145
                                                  43/113
6,393,759 B1 * 5/2002 Brown .................. A01M 1/023
                                                  43/113
(Continued)

FOREIGN PATENT DOCUMENTS

EP    0947134 A2   10/1999
EP    1457111 A1    9/2004
(Continued)

OTHER PUBLICATIONS

English-language translation of JP 11155455.*
English abstract for JP-H10146146-A.

*Primary Examiner* — Lisa L Tsang
(74) *Attorney, Agent, or Firm* — Fishman Stewart PLLC (57) ABSTRACT

The invention relates to an insect trap and more particularly to an insect trap which has been designed to facilitate the destruction of micro-organisms thereby countering odours and mitigating against the spread of germs. The trap may comprise a. a housing; b. a cover; c. one or a plurality of insect attracting lights; and d. an insect catching device and further includes a radiation emitting device such as a UVC lamp which emits radiation and is capable of destroying air-borne pathogens. The insect attractant lights heat the air which is convected and an air flow may be facilitated by louvered openings in the cover and an opening in the top of the trap so that the air flow circulates across the UVC lamp where the micro-organisms are killed.

21 Claims, 5 Drawing Sheets

(56) References Cited

U.S. PATENT DOCUMENTS

| | | | | |
|---|---|---|---|---|
| 6,574,914 | B2 * | 6/2003 | Smith | A01M 1/08 43/113 |
| 6,871,443 | B2 * | 3/2005 | Lambert | A01M 1/145 43/113 |
| 6,878,195 | B2 * | 4/2005 | Gibson | A61L 9/20 422/121 |
| 6,886,292 | B2 * | 5/2005 | Studer | A01M 1/026 43/112 |
| 2009/0288333 | A1 * | 11/2009 | Johnston | A01M 1/145 43/113 |
| 2010/0196214 | A1 * | 8/2010 | Graff | A61L 9/20 422/121 |
| 2011/0296740 | A1 * | 12/2011 | Yamada | A01M 1/04 43/107 |
| 2013/0312314 | A1 * | 11/2013 | Greening | A01M 1/145 43/114 |

FOREIGN PATENT DOCUMENTS

| | | | | |
|---|---|---|---|---|
| EP | 2269448 A1 * | 1/2011 | | A01M 1/145 |
| GB | 2459717 A * | 11/2009 | | A01M 1/04 |
| JP | H10146146 A | 6/1998 | | |
| JP | 11155455 A * | 6/1999 | | |
| WO | WO 9810643 A1 * | 3/1998 | | A01M 1/04 |

* cited by examiner

INSECT TRAP

CROSS-REFERENCES TO RELATED APPLICATIONS

This application claims priority to British patent application 1021293.4 filed on Dec. 15, 2010 and International patent application PCT/GB2011/001719 filed on Dec. 14, 2011, which are hereby incorporated by reference in their entirety.

TECHNICAL FIELD

The present invention relates to an insect trap and more particularly to an insect trap which has been designed to additionally provide protection against pathogens.

BACKGROUND OF THE INVENTION

Insect traps of various types are well known. A particularly common trap type, particularly for flying insects, comprises an insect attractant means, such as, for example a UV light source and an insect trapping means, such as, for example an adhesive board or paper contained in a housing. The flying insects are attracted to the trap, enter the housing through openings and get caught on the trapping means.

The traps are often fitted in areas where food is handled, such as kitchens and restaurants. Unfortunately, the captured insects die and decompose and thus can become a source of odour and can potentially spread germs.

Two Japanese patent publications disclose insect traps which address the issue of air sterilisation.

JP11155455 discloses a UV insecticidal tool enabling easy disposal of the dead bodies and remains of insects. It discloses the use or a sterilising lamp that is attached to the lower part of the insecticidal tool under the insect capturing lamp.

JP10146146 is consider the most pertinent prior art and it discloses a method and apparatus for insecticidal and bactericidal operation in which insects are killed by bringing them into contact with high voltage electrodes and bactericidal rays sterilise bacteria floating in the air. The device of embodiment 1 is cuboidal and utilises a pair of bactericidal lamps (4) to treat air passing from illuminating lamps which are disposed in the outer upper area of the high voltage electrodes (2). Barrier plates (8) limit irradiation of the air passing through air passage gaps (6) at the top of the device. In a second embodiment (diagrams 3 and 4) circular lamps are employed.

It is an object of the present invention to provide one or more traps which facilitate the destruction of micro-organisms thereby countering odours and mitigating against the spread of germs in traps employing insect capturing means.

In this regard the configuration and positioning of the insect attracting lights and UV lamp(s) relative to the insect capture means and the manner in which air is caused to circulate aids effective operation.

PRESENT INVENTION

According to the present invention there is provided a trap (10) for catching insects comprising
a. a housing (12);
b. a cover (14);
c. one or a plurality of insect attracting lights (16); and
d. an insect catching means (18);

characterised in that said trap further comprises a means (20) capable of destroying air-borne pathogens which is positioned towards the top (28) of the trap and wherein at least one insect attracting light is disposed at the bottom of the trap such that an air flow is generated from the bottom towards the means (20) capable of destroying air-borne pathogens where the air is treated or sterilized to destroy airborne pathogens picked up in the convecting air stream.

Preferably the means capable of destroying air-borne pathogens is one which generates UVC radiation although other means such as filters may be used.

Preferably, the source of the UVC radiation is one or a plurality of UVC lamps. To meet health and safety requirements such lamps are fitted with a UVC protective screen.

The UVC lamp(s) is/are positioned within the trap such that air circulating through the trap passes across it. In one embodiment a single lamp is positioned laterally across substantially a full width of the insect catching means so as to ensure that substantially all of the air circulating, as a result of convection, is exposed to radiation from the UVC lamp(s). Alternatively they may be disposed vertically to ensure a longer contact time with the air as it flows along the full length of the lamp.

In a first embodiment a single UVC lamp is positioned towards the top of the trap such that it acts upon air which has passed across or over the majority of the insect catching means.

The trap may comprise one or a plurality of glue boards. In a preferred embodiment the trap comprises a first glue board, positioned on the back housing behind the insect attractant lights, and a second glue board positioned underneath, to catch falling insects.

In a preferred embodiment the cover comprises a plurality of openings allowing insects to enter the trap. These are most preferably elongate openings which traverse the cover laterally. Such a configuration, optionally with angled blades, helps to facilitate circulation of air across the insect capture means.

The trap may additionally comprise a sized opening at the top to allow heat generated by the lamps to escape. It can also be used to help control the air flow.

Preferably the cover is made of a translucent or opaque material.

Preferably the trap comprises light reflectors behind the lamps.

Like in PCT/GB2009/001097, the trap may benefit from the features disclosed therein, such as, a fluorescent high frequency electronic ballast and shields, which sealably protect the electrics from water ingress where the lights connect to associated electrical fittings.

Supporting the lights on a separate perimeter frame, which can be swung away from a back housing, allows easier access to both the lights and the insect catching means. In particular, it avoids a requirement when mounting the trap to provide sufficient clearance above the trap to allow for fitting of the insect catching means. The perimeter frame comprises ducting or channels which communicate with the back housing in a manner which prevents water ingress. It is through these channels that the electric wiring is ducted and the channels are then appropriately sealed.

Preferably, the back housing is shaped so that it can also receive fluorescent high frequency electronic ballast. Such ballast is carbon friendly, provides for flicker free start of the lights, offers higher UV output and avoids the need for a starter.

The back housing is designed to comprise or allow for the fitting of one or more of, for example, an electrical IEC socket, a heat sink, mounting means, air vents and cable stowage.

Preferably the cover is translucent and comprises an innermost surface which helps maximise UV emission from the trap as claimed in EP1457111.

More preferably it is adapted to ensure the lights are not readily visible through the cover as claimed in EP0947134. To this end, in a particularly favoured embodiment the cover comprises openings angled to prevent the lights being visible when viewed substantially perpendicularly to a plane of the back housing. A more favoured arrangement is one in which the openings are paired about a centre point to provide a downward and upward inflexion respectively. Such an arrangement helps to draw air in at the bottom of the trap.

The various aspects of the invention will be described further, by way of example, with reference to the following figures in which.

DETAILED DESCRIPTION

Referring to the Figs an insect trap (10) according to the invention comprises five basic components:

a housing (12);
a cover (14)
one or a plurality of insect attracting lights (16a,b,c)
an insect catching means (18a,b); and
a means (20) for destroying air-borne pathogens.

Figure 3:
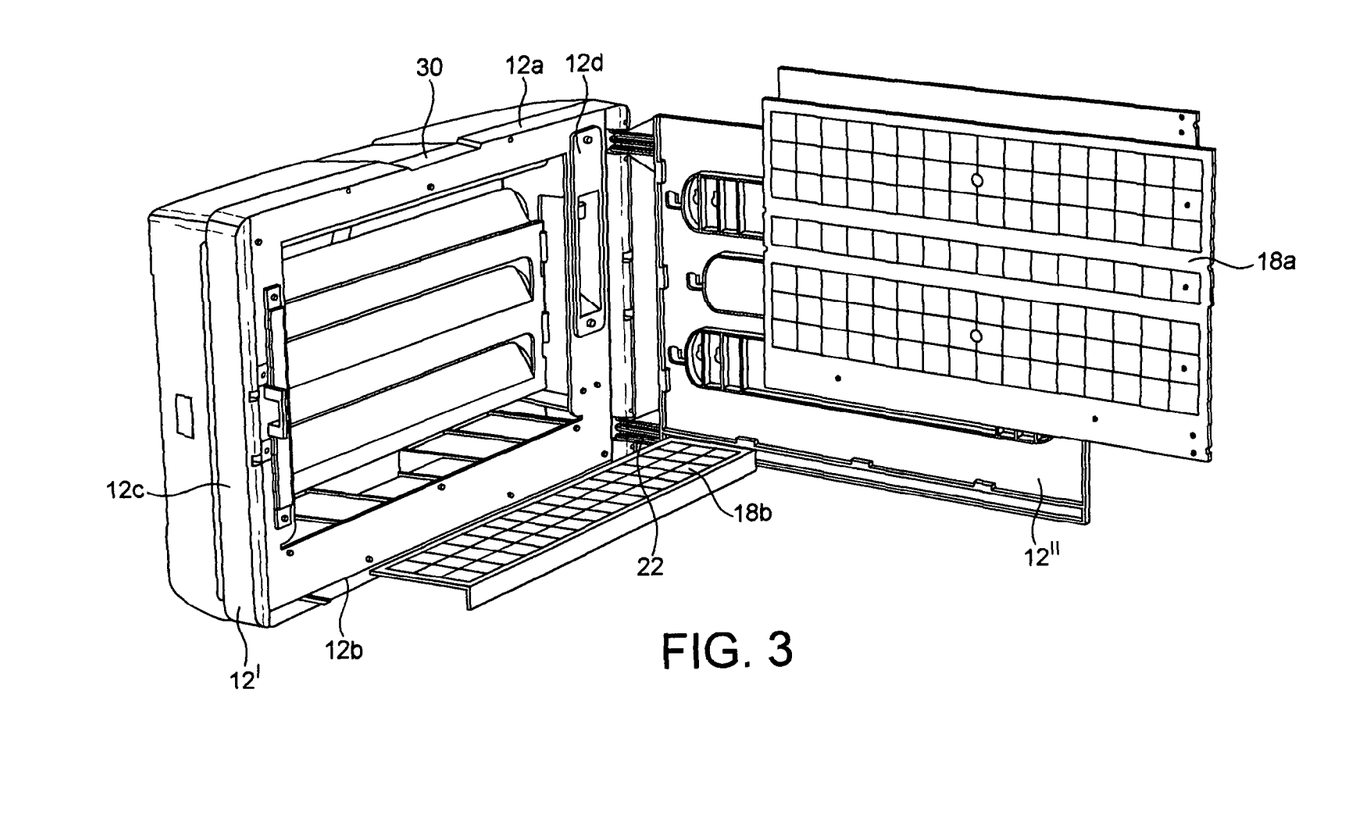
FIG. 3 is perspective view of the insect trap with the housing hinged open to show the insect catching means.

In the exemplifying embodiment the frame (12) comprises a perimeter frame (12') which is hinged to a back frame (12"). Such a frame allows the insect attracting lights to be carried in a manner allowing ease of access as disclosed in PCT/GB2009/001097. The perimeter frame (12') is best illustrated in FIG. 3 and comprises upper (12a) and lower (12b) frame members and two side members (12c; 12d). The perimeter frame (12') is swing, swivel or hinge mounted to the back frame (12") via a swing mechanism (22).

A plurality of 15 W or 25 W UV lights (16), three are illustrated in the example, are connected to paired electrical fittings and wiring which runs in channels or conduits which are sealed by rubber or silicon gaskets and enclosed by fascia plates such that they provide rigidity to the moulded plastics frame in a manner disclosed in PCT/GB2009/001097.

Behind each light (16a, b, c) there is provided a reflector (24a, b, c) which is held in place by stops which enable the reflectors to be sprung mounted thereby facilitating ease of removal for cleaning. An insect capturing means (18a, b), in the form of a back glue board (18a) and a base glue board (18b) can be easily fitted between the back frame (12") and the perimeter housing (12').

Figure 1:
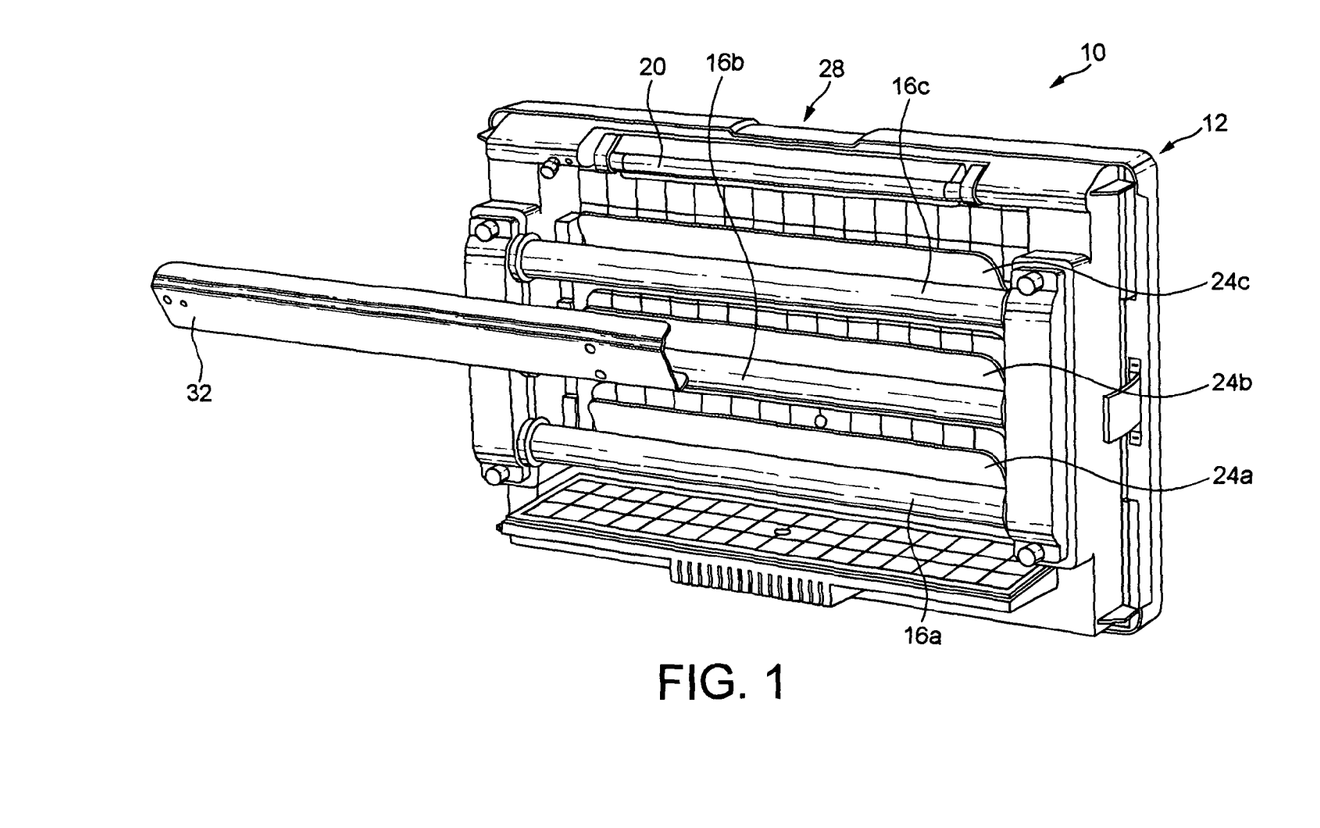
FIG. 1 is perspective view of an insect trap according to the invention with the cover removed and the UVC shield displaced.

The cover (14) is made of a translucent material and has an innermost surface which is shaped or roughened to maximise the transmission of UV light as set out in EP1457111. The openings (26) which allow insects in maybe simple apertures as illustrated or louvered or angled to prevent the lights (16) being visible when viewed substantially perpendicularly to the normal plane of the back housing (12a). The general principle of maintaining a pleasant appearance of trap is set out in EP0947134 but the use of louvers is a further improvement in this regard. In particular, the louver openings (26) are paired about a centre axis (x-x) to provide a downward and upward inflexion respectively of between 30 and 60°. The apertures whether planar or louvered help facilitate air flow in the trap and air moves upwards by convection as it is heated by the lights (16). Thus, an air flow is created from the bottom, over base glue board (18b) and across back glue board (18a) towards the UVC lamp (20) where it is treated or sterilized to destroy airborne pathogens picked up in the convecting air stream. The UVC lamp has associated with it a safety screen (32) which is fitted in front thereof. In FIG. 1 it is shown displaced for clarity.

At the top (28) of the trap there is a sized opening (30) which allows hot air to escape. This assists in ensuring the air flows across the UVC lamp (20) for a period sufficient to destroy airborne pathogens. The skilled person will appreciate that to increase the contact time between the air and the UVC lamp, the lamp (or lamps) can be orientated in different directions, for example longitudinally (from top to bottom) as opposed to transverse (across), thereby increasing contact time as the air flows across the lamp from the bottom of the trap to the top.

As described in PCT/GB2009/001097 the trap has many of the features and benefits described therein and which are not therefore disclosed in detail herein. Thus, the trap is suited to jet washing (to IP65 requirements) and shields (34) are fitted around of the light where it connects to electrical fittings. In this manner two single shields (34) can be removed to access a plurality of lights. A similar shield may be used about the UVC lamp.

EXAMPLES

Figure 2:
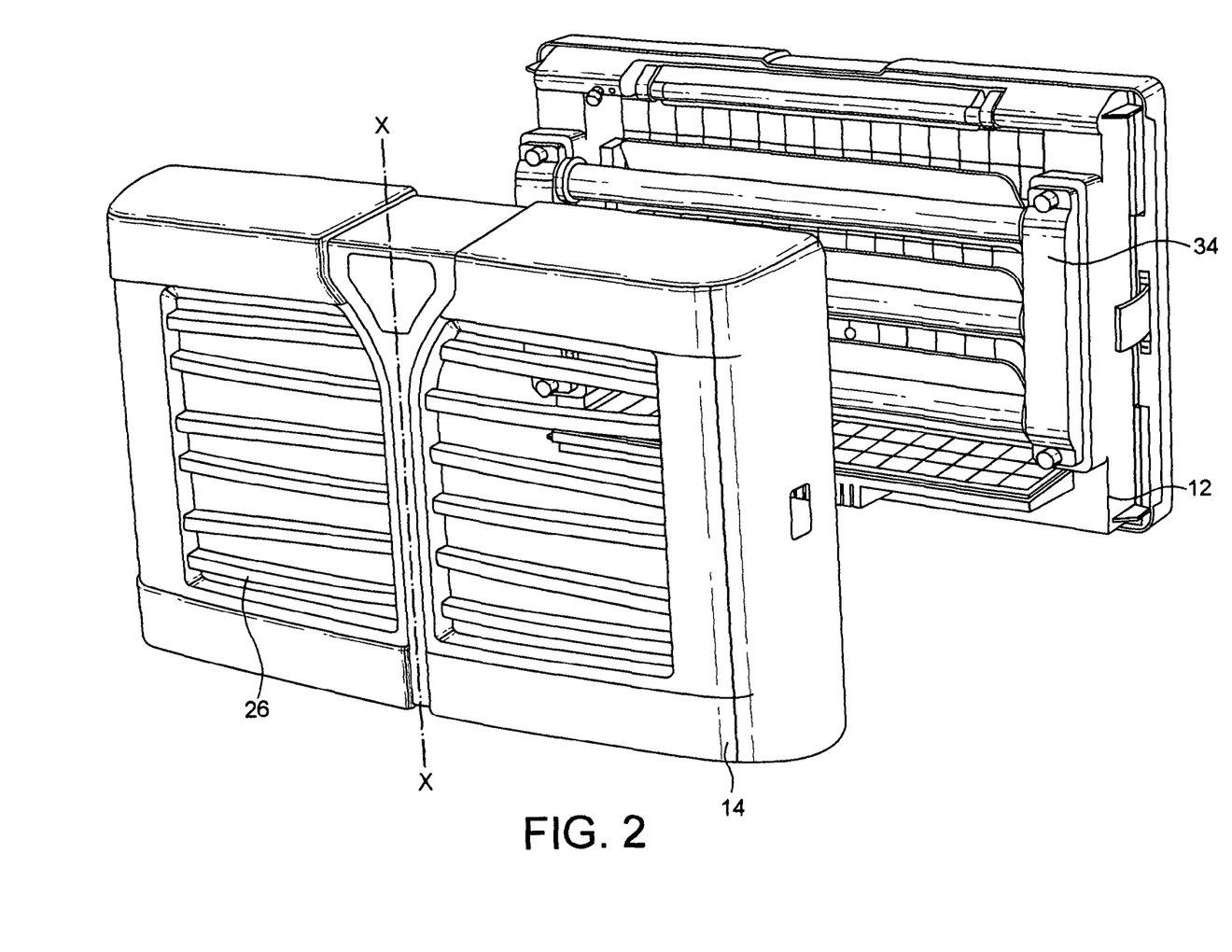
FIG. 2 is perspective view of an insect trap according to the invention with the cover shown displaced from the housing and the UVC lamp and cover removed.

In order to test the efficacy of the trap arrangement, the trap described with reference to FIGS. 1-3 was subjected to a trial as described below, in order to determine if any microorganisms derived from fly corpses were prevented from contaminating the atmosphere of a room by the incorporation of a UV lamp into the trap.

Two microbial sources were employed. In a first trial, a fungal lawn of *Aspergillus niger* was grown on agar plates which were placed at the bottom of the trap. It was anticipated that this would provide a consistent and abundant source of airborne spores. A second trial involved the location of 300 dead house flies which had been sprayed with a *Bacillus circulans* (Bacterial) culture at the bottom of the trap.

Each trial involved measuring the level of fungal or bacterial contamination in a 25 $m^2$ vented space over a 48 hour sampling period at 4 hour intervals. A control trap had a white light source, whilst the active trap utilised a UV source.

Results

Figure 4:
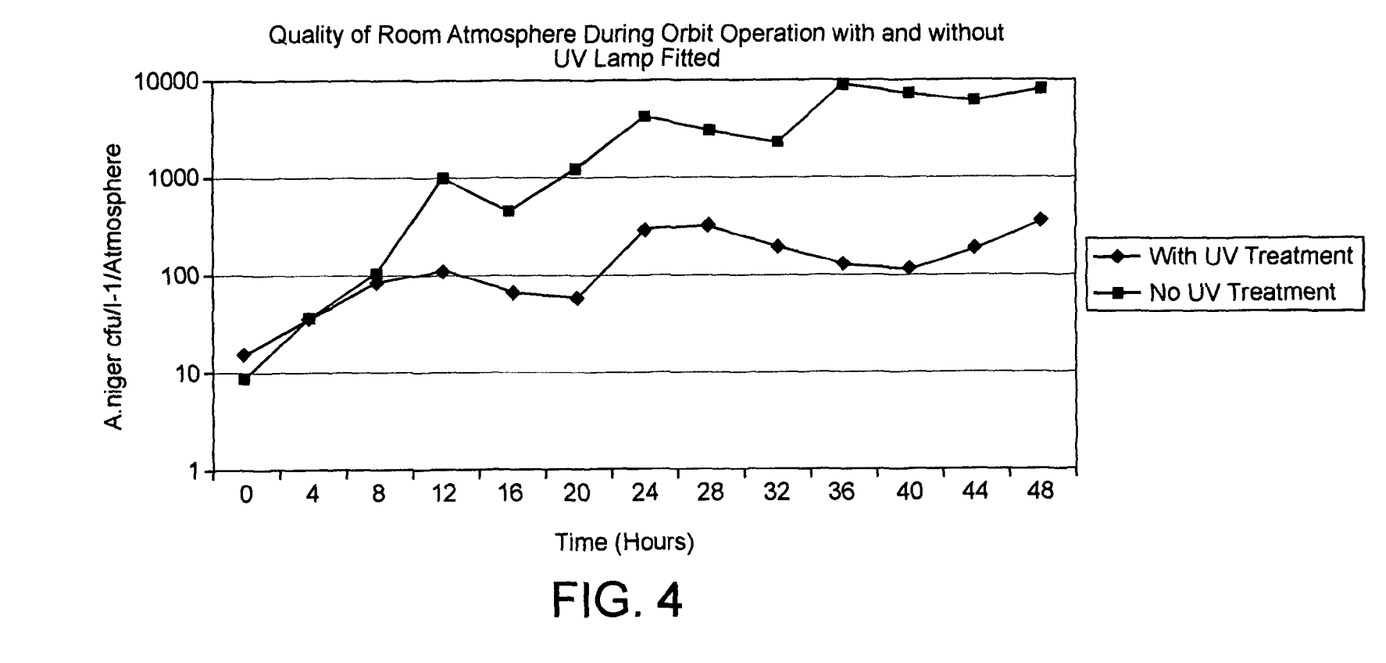
FIG. 4 is a graph showing the levels of *A. niger* present in the atmosphere over time with an insect trap with and without a UV lamp fitted.
Figure 5:
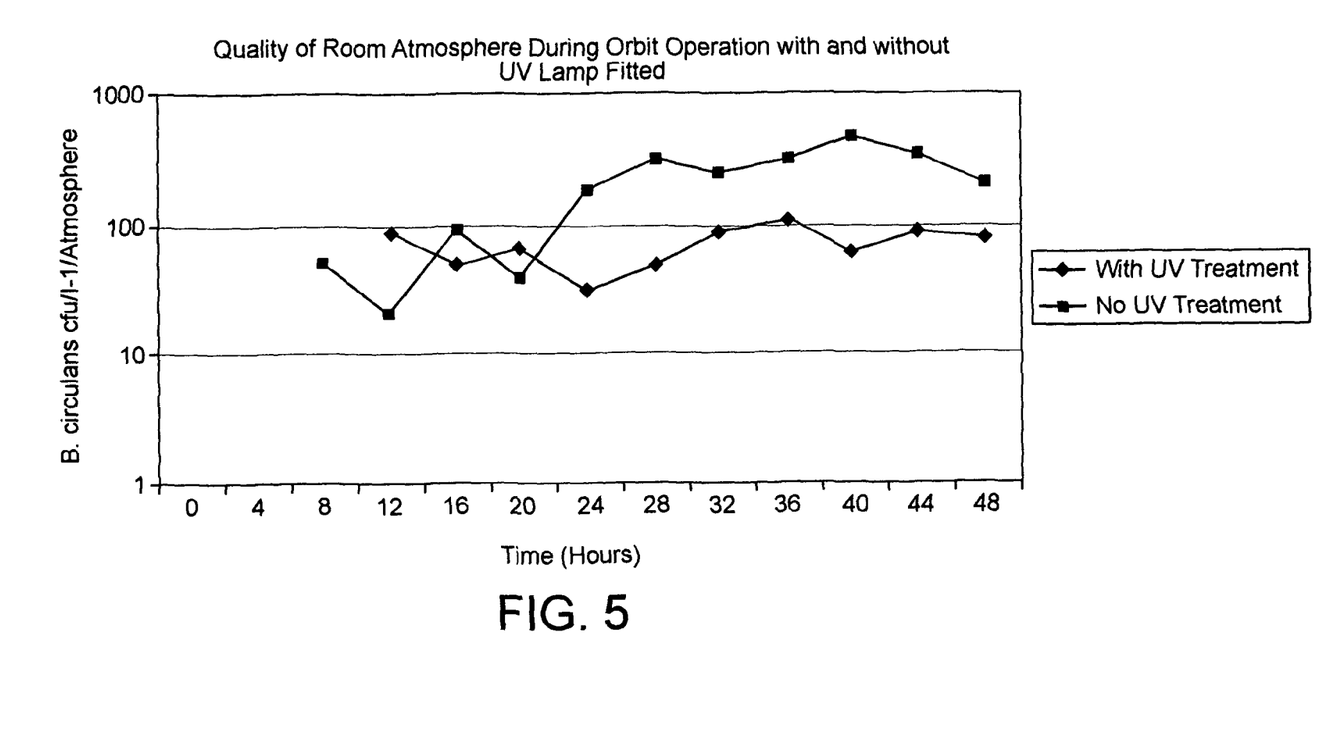
FIG. 5 is a graph showing the levels of *B. circulans* present in the atmosphere over time with an insect trap with and without a UV lamp fitted.

The results of the respective experiments are given in Table 1 and Table 2 and these are shown graphically in FIGS. 4 and 5.

CONCLUSIONS

The results shown in the tables and graphs indicate that UV dosing reduced fungal emissions by 95% (Table 1 and FIG. 4) and bacterial emissions by 65% (Table 2 and FIG. 5).

TABLE 1

Atmospheric levels of Aspergillus niger detected during operation of Orbit devices fitted with a UV lamp or White light lamp (Internal device challenge with an *Aspergillus niger* lawn)

| | Hours | | | | | | | | | | | | | |
|---|---|---|---|---|---|---|---|---|---|---|---|---|---|---|
| Treatment | 4 | 8 | 12 | 16 | 20 | 24 | 28 | 32 | 36 | 40 | 44 | 48 | | MEAN |
| UV | 17 | 40 | 90 | 110 | 70 | 60 | 300 | 340 | 200 | 130 | 110 | 200 | 390 | 158 |
| Control | 9 | 36 | 103 | 940 | 460 | 1200 | 4300 | 3100 | 2300 | 9200 | 7200 | 6300 | 8300 | 3342 |

Mean Percent Difference reduction due to UV treatment over 48 hours: 95
All data Colony forming units per Litre of atmosphere

TABLE 2

Atmospheric levels of TOTAL VIABLE COUT detected during operation of Orbit devices fitted with a UV lamp or White light lamp (Internal device 300 House flies spiked with *Bacillus circulans*)

| | Hours | | | | | | | | | | | | |
|---|---|---|---|---|---|---|---|---|---|---|---|---|---|
| Treatment | 4 | 8 | 12 | 16 | 20 | 24 | 28 | 32 | 36 | 40 | 44 | 48 | MEAN |
| UV | | 90 | 50 | 70 | 30 | 50 | 90 | 110 | 60 | 90 | 80 | | 55 |
| Control | 50 | 20 | 90 | 40 | 180 | 300 | 260 | 310 | 460 | 340 | 200 | | 173 |

Mean Percent Difference reduction due to UV treatment over 48 hours: 68
All data Colony forming units per Litre of atmosphere

The invention claimed is:

1. A trap for catching insects comprising:
    a housing including a perimeter frame hinged to a back frame;
    a cover;
    at least one insect attracting light arranged at a bottom of the housing between the cover and the back frame;
    an insect catching device arranged between the housing and the at least one insect attracting light, the insect catching device including a base glue board disposed at the bottom of the housing and a back glue board disposed behind the at least one insect attracting light with respect to the cover;
    at least one UVC radiation emitting device capable of destroying air-borne pathogens, the at least one UVC radiation emitting device positioned proximate to a top of the housing on the perimeter frame and arranged across the back glue board; and
    a protective screen fitted over the at least one radiation emitting device;
    wherein the housing has a sized opening positioned centrally at the top in proximity to the back glue board for facilitating a controlled flow of air such that an air flow is generated at least in part by convection from the bottom of the housing via the at least one insect attracting light over the base glue board and across the back glue board to convey air-borne pathogens derived from trapped insects towards the at least one UVC radiation emitting device disposed proximate to the top of the housing and positioned laterally across substantially a full width of the insect catching device to ensure that substantially all of the air flow circulating at least partially via convection is exposed to UVC radiation from the at least one UVC radiation emitting device for a period sufficient to at least one of sterilize and destroy air-borne pathogens picked up in the convection air flow.

2. The trap of claim 1, wherein the at least one insect attracting light includes a UV light.

3. The trap of claim 1, wherein the at least one UVC radiation emitting device includes at least one UVC lamp.

4. The trap of claim 3, wherein the protective screen has a structure fitted to cover a length of the at least one UVC lamp laterally across the housing, and wherein the protective screen is positioned in front of the at least one UVC lamp with respect to the cover.

5. The trap of claim 3, wherein the perimeter frame mounts the at least one UVC lamp and the insect catching device including the base glue board and the back glue board is arranged between the perimeter frame and the back frame such that the convection air flow passes along the insect catching device and across the at least one UVC lamp.

6. The trap of claim 1, wherein the at least one insect light includes a plurality of UV lights extending laterally across the back frame and spaced apart from one another longitudinally in a direction running from the bottom to the top of the housing.

7. The trap of claim 1, wherein the cover is composed of translucent material or opaque material.

8. The trap of claim 1, wherein the cover includes a plurality of louvered openings extending laterally across the cover, the plurality of louvered openings disposed paired about a center axis running from the bottom to the top of the housing to provide an upward inflection and a downward inflection, respectively, where the upward inflection and the downward inflection are angled obliquely to the center axis.

9. The trap of claim 1, wherein the cover includes a plurality of openings traversing the cover laterally to facilitate circulation of air in the housing.

10. The trap of claim 9, wherein the cover constitutes one of a translucent and opaque material.

11. The trap of claim 1, wherein the housing includes a fluorescent high frequency electronic ballast.

12. An insect trapping device, comprising:
a cover including at least one opening allowing insects to enter; and
a housing including:
at least one insect attracting light disposed in a lower portion of the housing;
an insect catching device disposed in the housing behind the at least one insect attracting light with respect to the cover;
at least one radiation emitting device capable of destroying air-borne pathogens fitted with a protective screen, the at least one radiation emitting device disposed in an upper portion of the housing and extending laterally across substantially a full width of the upper portion of the housing;
wherein the at least one insect attracting light is configured to facilitate an air flow in the housing so that the air flow moves over the insect catching device to convey air-borne pathogens derived from trapped insects upwards towards the at least one radiation emitting device by convection, where the air flow is at least one of treated and sterilized to destroy air-borne pathogens picked up in the air flow; and
wherein the at least one opening includes a plurality of louvered openings extending laterally across the cover, the plurality of louvered openings disposed paired about a center axis running from the lower portion to the upper portion of the housing to provide an upward inflection and a downward inflection, respectively, where the upward inflection and the downward inflection are angled obliquely to the center axis.

13. The device of claim 12, wherein the plurality of louvered openings are provided by angled blades defined by the cover and paired about the center axis.

14. The device of claim 12, wherein the plurality of louvered openings are paired about the center axis to provide a first set of louvered openings having the downward inflection and a second set of louvered openings having the upward inflection.

15. The device of claim 12, wherein the at least one radiation emitting device includes a UVC lamp configured to emit UVC radiation.

16. The device of claim 12, further comprising a light reflector disposed behind the at least one insect attracting light.

17. The device of claim 12, wherein the housing further includes a perimeter frame and a back frame, the perimeter frame disposed between the back frame and the cover, and wherein the at least one insect attracting light and the at least one radiation emitting device are mounted on the perimeter frame, and the insect catching device is mounted between the perimeter frame and the back frame.

18. The device of claim 17, further comprising a sized opening arranged at a top of the housing above the at least one radiation emitting device to facilitate controlling the air flow.

19. A trap for catching insects, comprising:
a cover including at least one opening;
a housing mounted to the cover, wherein the housing includes a perimeter frame and a back frame, and wherein the perimeter frame is disposed between the cover and the back frame;
an insect attracting light mounted on the perimeter frame and positioned proximate to a bottom of the housing;
a UVC radiation emitting device capable of destroying air-borne pathogens, the UVC radiation emitting device mounted on the perimeter frame and positioned proximate to a top of the housing;
a protective screen arranged to cover the UVC radiation emitting device, the protective screen disposed between the perimeter frame and the cover;
an insect catching device including a back glue board mounted between the perimeter frame and the back frame and a base glue board disposed at the bottom of the housing;
a sized opening disposed centrally at the top of the housing in proximity to the back glue board to facilitate a controlled flow of air across the UVC radiation emitting device;
wherein the insect attracting light facilitates an air flow that is generated at least partially by convection from the bottom of the housing over the base glue board and across the back glue board to convey air-borne pathogens derived from trapped insects towards the UVC radiation emitting device disposed proximate to the top of the housing and positioned laterally across the insect catching device to ensure that substantially all of the air flow circulating via convection is exposed to radiation for a period sufficient to at least one of sterilize and destroy air-borne pathogens picked up in the air flow; and
wherein the protective screen has an elongate structure fitted over the UVC radiation emitting device and arranged to shield in front of the UVC radiation emitting device with respect to the cover.

20. The trap of claim 19, wherein the at least one opening of the cover includes a plurality of louvered openings structured to facilitate circulation of the air flow across the back glue board, and wherein the plurality of louvered openings are paired about a center axis of the cover extending transverse to the UVC radiation emitting device to provide a first set of louvered openings having a downward inflection and a second set of louvered openings having an upward inflection, the downward inflection and the upward inflection respectively angled obliquely to the center axis.

21. The trap of claim 19, wherein the protective screen further defines two transversely projecting ends fitted respectively fitted above and below the UVC radiation emitting device with respect to the top of the housing.

* * * * *